(12) United States Patent
Lalli et al.

(10) Patent No.: US 10,456,016 B2
(45) Date of Patent: Oct. 29, 2019

(54) APPLICATOR FOR A SPECULUM ACCESSORY SLEEVE AND USE THEREOF

(71) Applicant: Ceek Enterprises, Portland, OR (US)

(72) Inventors: Maria Lalli, Portland, OR (US); Christian Freissler, Portland, OR (US); Katie Lee, Portland, OR (US); Ute Peppersack, Cologne (DE)

(73) Assignee: CEEK Enterprises, Portland, OR (US)

( * ) Notice: Subject to any disclaimer, the term of this patent is extended or adjusted under 35 U.S.C. 154(b) by 0 days.

(21) Appl. No.: 15/588,439

(22) Filed: May 5, 2017

(65) Prior Publication Data

US 2018/0317746 A1    Nov. 8, 2018

(51) Int. Cl.
  *A61B 1/00*    (2006.01)
  *A61B 1/303*   (2006.01)
  *A61B 50/30*   (2016.01)

(52) U.S. Cl.
  CPC ........ *A61B 1/0014* (2013.01); *A61B 1/00135* (2013.01); *A61B 1/00142* (2013.01); *A61B 1/303* (2013.01); *A61B 50/30* (2016.02); *A61B 1/00103* (2013.01)

(58) Field of Classification Search
  CPC . A61B 1/00142; A61B 1/303; A61B 1/00–32; A61B 1/0014
  See application file for complete search history.

(56) References Cited

U.S. PATENT DOCUMENTS

| | | |
|---|---|---|
| 55,511 A | 6/1866 | Lentz |
| 977,489 A | 12/1910 | Unruh |
| 1,969,671 A | 8/1934 | Nelson |
| 2,083,573 A | 6/1937 | Morgan |
| 2,123,343 A | 7/1938 | Rightsell |
| 2,324,485 A | 7/1943 | Chamberlain, Jr. |
| 2,509,241 A | 5/1950 | Mende |
| 2,670,736 A | 3/1954 | Dunkelberger |
| 2,714,886 A | 8/1955 | Castelli |
| 2,884,925 A | 5/1959 | Meynier, Jr. |
| 3,139,886 A | 7/1964 | Tallman |
| 3,841,317 A | 10/1974 | Awais |
| 3,857,395 A | 12/1974 | Johnson et al. |
| 3,885,563 A | 5/1975 | Johnson et al. |

(Continued)

FOREIGN PATENT DOCUMENTS

| | | |
|---|---|---|
| CN | 201595813 U | 10/2010 |
| CN | 201996970 U | 10/2011 |

(Continued)

OTHER PUBLICATIONS

International Search Report and Written Opinion for Application No. PCT/US2016/069048, dated Jul. 11, 2017.

*Primary Examiner* — Nicholas J Plionis
(74) *Attorney, Agent, or Firm* — Mintz, Levin, Cohn, Ferris, Glovsky and Popeo, P.C.

(57) ABSTRACT

An applicator for positioning a sleeve accessory on a medical speculum, and a method for using the applicator, is provided. The applicator has a flat, oblong shape with a distal end and a proximal end, the proximal end being broader than the distal end. The distal end of the applicator includes a first prong and a second prong. At least a portion of the distal end of the applicator is configured to slide into a lumen of a sleeve accessory to facilitate positioning of the sleeve accessory on a medical speculum.

14 Claims, 8 Drawing Sheets

(56) References Cited

U.S. PATENT DOCUMENTS

| | | |
|---|---|---|
| 4,004,591 A | 1/1977 | Freimark |
| 4,010,751 A | 3/1977 | Ring |
| 4,356,817 A | 11/1982 | McKibben et al. |
| 4,428,370 A | 1/1984 | Keely |
| 4,492,220 A | 1/1985 | Hayes |
| 4,597,382 A | 7/1986 | Perez, Jr. |
| 4,676,773 A | 6/1987 | Sheldon |
| 4,735,621 A | 4/1988 | Hessel |
| 4,805,604 A | 2/1989 | Spery |
| 4,807,600 A | 2/1989 | Hayes |
| 4,834,077 A | 5/1989 | Sun |
| 4,857,175 A | 8/1989 | Spinnler |
| 4,867,176 A | 9/1989 | Lash |
| 4,945,923 A | 8/1990 | Evans et al. |
| 4,976,273 A | 12/1990 | Hessel |
| 4,981,147 A | 1/1991 | Barnett |
| 4,993,433 A | 2/1991 | Reddy |
| 5,007,409 A | 4/1991 | Pope |
| 5,041,080 A | 8/1991 | Shimatani et al. |
| 5,083,414 A | 1/1992 | Wu |
| 5,094,250 A | 3/1992 | Hessel |
| 5,135,475 A | 8/1992 | Nakanishi et al. |
| 5,156,165 A | 10/1992 | Wu |
| 5,179,936 A | 1/1993 | O'Hara et al. |
| 5,193,555 A | 3/1993 | Richardson et al. |
| 5,209,241 A | 5/1993 | Hardy |
| 5,243,966 A | 9/1993 | Ng |
| 5,347,995 A | 9/1994 | Slater et al. |
| 5,377,667 A | 1/1995 | Patton et al. |
| 5,433,219 A | 7/1995 | Spery |
| 5,505,690 A | 4/1996 | Patton et al. |
| 5,540,658 A | 7/1996 | Evans et al. |
| 5,598,852 A | 2/1997 | Spery |
| 5,622,185 A | 4/1997 | Richardson et al. |
| 5,623,946 A | 4/1997 | Hessel |
| 5,687,741 A | 11/1997 | Torger |
| 5,716,329 A | 2/1998 | Dieter |
| 5,785,648 A | 7/1998 | Min |
| 5,868,668 A | 2/1999 | Weiss |
| 5,992,415 A | 11/1999 | Alla et al. |
| 6,019,743 A | 2/2000 | Cole et al. |
| 6,024,696 A | 2/2000 | Hoftman et al. |
| 6,036,638 A | 3/2000 | Nwawka |
| 6,048,308 A | 4/2000 | Strong |
| 6,095,998 A | 8/2000 | Osborn et al. |
| 6,096,046 A | 8/2000 | Weiss |
| 6,174,282 B1 | 1/2001 | Tan |
| 6,186,973 B1 | 2/2001 | Buzot |
| 6,248,089 B1 | 6/2001 | Porat |
| 6,254,566 B1 | 7/2001 | Buck et al. |
| 6,280,379 B1 | 8/2001 | Resnick |
| 6,287,251 B1 | 9/2001 | Tan |
| 6,302,862 B1 | 10/2001 | Osborn et al. |
| 6,341,607 B1 | 1/2002 | Couvreur |
| 6,347,243 B1 | 2/2002 | Fraden |
| 6,354,995 B1 | 3/2002 | Hoftman et al. |
| 6,395,012 B1 | 5/2002 | Yoon et al. |
| 6,416,467 B1 | 7/2002 | McMillin et al. |
| 6,428,474 B1 | 8/2002 | Weiss |
| 6,432,048 B1 | 8/2002 | Francois |
| 6,436,033 B2 | 8/2002 | Tan |
| 6,508,780 B1 | 1/2003 | Edgett et al. |
| 6,902,530 B1 | 6/2005 | Pianka |
| 6,939,289 B2 | 9/2005 | Zunker et al. |
| 7,047,975 B2 | 5/2006 | Austin et al. |
| 7,063,664 B2 | 6/2006 | Mohajer |
| 7,105,007 B2 | 9/2006 | Hibler |
| 7,172,573 B1 | 2/2007 | Lamb |
| D558,871 S | 1/2008 | Osterberg |
| 7,322,358 B2 | 1/2008 | Tam et al. |
| 7,338,462 B2 | 3/2008 | Minoguchi et al. |
| 7,392,807 B2 | 7/2008 | Osterberg |
| D593,195 S | 5/2009 | Osterberg |
| 7,665,893 B2 | 2/2010 | Buchalter |
| 7,798,986 B2 | 9/2010 | Melvin et al. |
| 7,810,500 B2 | 10/2010 | Osterberg |
| 7,815,594 B2 | 10/2010 | Dougherty et al. |
| 7,896,806 B2 | 3/2011 | Shah et al. |
| 7,918,004 B2 | 4/2011 | Melvin et al. |
| 8,062,245 B2 | 11/2011 | Gann et al. |
| 8,075,512 B2 | 12/2011 | Sargent et al. |
| 8,083,673 B2 | 12/2011 | Rosen |
| 8,162,872 B2 | 4/2012 | Loyd et al. |
| 8,256,423 B2 | 9/2012 | Osterberg |
| 8,435,205 B2 | 5/2013 | Arora et al. |
| 8,449,491 B2 | 5/2013 | Hasse et al. |
| 8,449,492 B2 | 5/2013 | Sargent et al. |
| 8,460,187 B2 | 6/2013 | Bouquet |
| 8,485,196 B2 | 7/2013 | Osterberg |
| 8,539,660 B2 | 9/2013 | Melvin et al. |
| 8,652,035 B2 | 2/2014 | Steigerwald |
| 8,734,414 B2 | 5/2014 | Winkel et al. |
| 8,747,308 B2 | 6/2014 | Muzzammel |
| 8,876,711 B2 | 11/2014 | Lin et al. |
| 8,926,547 B2 | 1/2015 | Arora et al. |
| 8,979,751 B2 | 3/2015 | George |
| 8,979,851 B2 | 3/2015 | Fallin et al. |
| 9,132,043 B2 | 9/2015 | Winkel et al. |
| 9,186,282 B2 | 11/2015 | Ito et al. |
| 9,233,029 B2 | 1/2016 | Gann et al. |
| 9,283,122 B2 | 3/2016 | Taniguchi et al. |
| 2003/0069477 A1 | 4/2003 | Raisman et al. |
| 2004/0231772 A1* | 11/2004 | Leonard ............ A61B 1/00062 150/161 |
| 2005/0021069 A1 | 1/2005 | Feuer et al. |
| 2005/0124860 A1 | 6/2005 | Mohajer |
| 2005/0192482 A1 | 9/2005 | Carpenter et al. |
| 2005/0197615 A1 | 9/2005 | Gann et al. |
| 2005/0273044 A1 | 12/2005 | Gann et al. |
| 2005/0277867 A1 | 12/2005 | Minoguchi et al. |
| 2006/0047285 A1 | 3/2006 | Fields |
| 2006/0224043 A1* | 10/2006 | Guinan ................ A61B 1/303 600/220 |
| 2007/0032758 A1 | 2/2007 | Chase et al. |
| 2007/0032814 A1 | 2/2007 | Hibler |
| 2008/0114210 A1 | 5/2008 | Shah et al. |
| 2008/0242938 A1 | 10/2008 | Larkin |
| 2008/0262407 A1 | 10/2008 | Chase et al. |
| 2009/0099422 A1* | 4/2009 | George ................ A61B 1/32 600/214 |
| 2011/0009803 A1 | 1/2011 | Dougherty et al. |
| 2011/0040234 A1 | 2/2011 | Chaffringeon |
| 2011/0237902 A1 | 9/2011 | Rosen |
| 2012/0220918 A1 | 8/2012 | Chaffringeon |
| 2013/0197314 A1 | 8/2013 | Eakin |
| 2014/0109915 A1 | 4/2014 | Reddy et al. |
| 2014/0163322 A1 | 6/2014 | Mehta |
| 2015/0057502 A1 | 2/2015 | George |
| 2015/0112148 A1 | 4/2015 | Bouquet |
| 2015/0290440 A1 | 10/2015 | Redol |
| 2016/0029882 A1* | 2/2016 | Young ................ A61B 1/303 600/222 |
| 2017/0181605 A1 | 6/2017 | Lalli et al. |

FOREIGN PATENT DOCUMENTS

| | | |
|---|---|---|
| EP | 0966223 A1 | 12/1999 |
| EP | 1833376 A2 | 9/2007 |
| GB | 2424585 A | 10/2006 |
| WO | WO-9612437 A1 | 5/1996 |
| WO | WO-98/33431 A1 | 8/1998 |
| WO | WO-2017117313 A2 | 7/2017 |

* cited by examiner

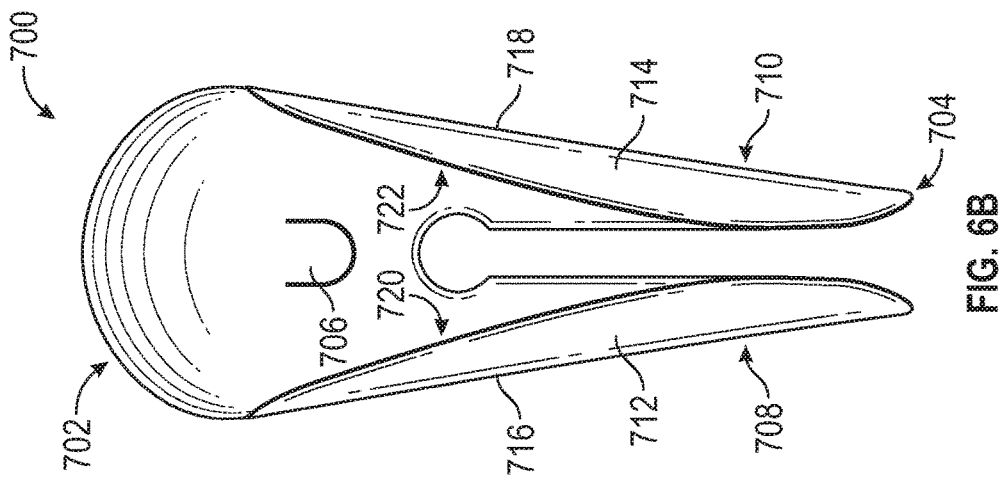
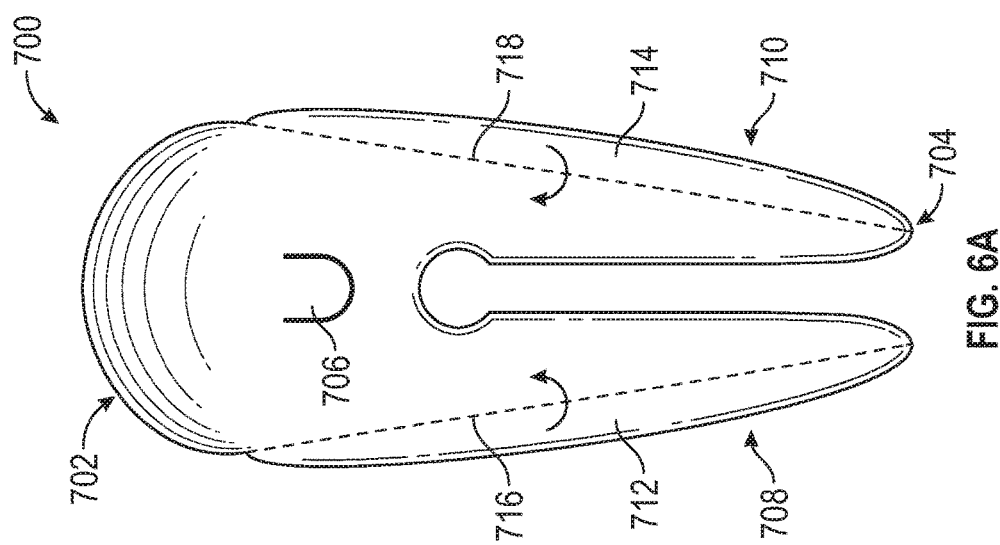

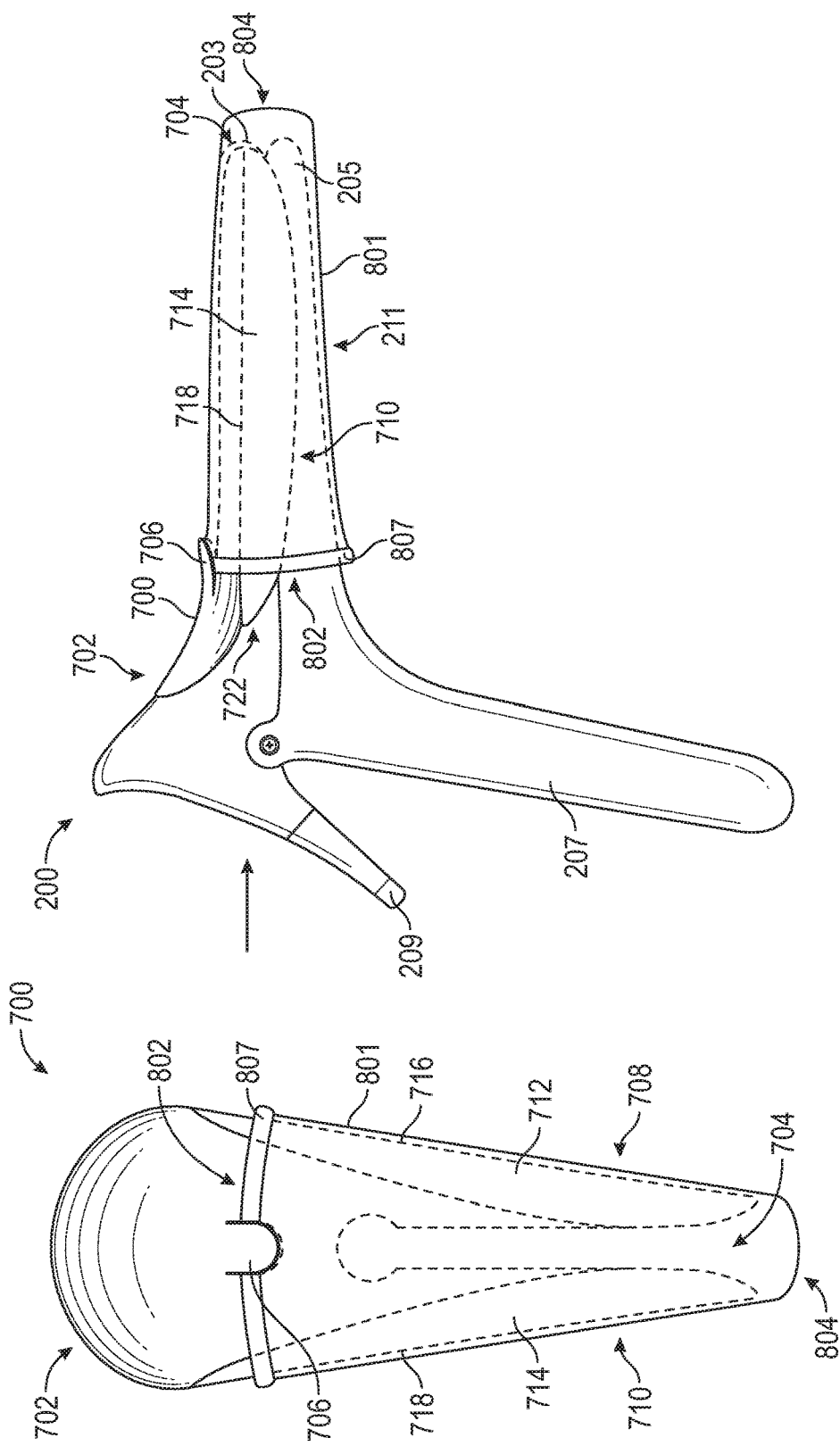

APPLICATOR FOR A SPECULUM ACCESSORY SLEEVE AND USE THEREOF

BACKGROUND

The present invention relates generally to the field of a medical speculum, and more particularly to an applicator for applying a sleeve to a medical speculum.

A speculum is a medical tool used to provide visualization into a body cavity. Speculums or specula are traditionally used for viewing and accessing the vaginal cavity for gynecology patients. The traditional speculum consists of two blades with a hinge and a handle. The blades are inserted into the body cavity in a closed position, and separated by squeezing two pieces of the handle together or applying force to a lever attached to the handle, thereby dilating the vagina and providing visualization of and accessibility to the vagina, the cervix, and surrounding areas. Once opened, the speculum can be locked in an open position, e.g., by using a screw-based mechanism so an operator (e.g., physician, nurse, mid-wife, etc.) does not need to continue squeezing the pieces of the handle or the lever during the inspection. The operator can then proceed with inspecting the vagina, conducting a Pap smear, or any other medical procedures that may need to be provided.

The double blade design of speculum devices has been in use since the 1800s, and few changes have been made to the original design. The biggest changes with the double-blade design have been changes in the material from metal to plastic and the addition of internal lighting on some models of the speculum so that the operator does not have to rely on external lighting to gain a clear view of the vagina and the cervix.

There are drawbacks with the traditional two blade design. For one, tissue can enter between the blades once they are opened inside the vaginal cavity, a common occurrence that providers characterize as "side wall encroachment." Women, especially obese women, women with multiple vaginal births, or those with vaginal laxity, may have extra tissue in the side walls of the vagina that may fall into the space between the two blades once opened. This can cause problems for operators, particularly in providing clear visualization of the vagina and cervix, which potentially limits the effectiveness of the procedure. Furthermore, with all patients, when trying to close the speculum blades, tissue and/or pubic hair may become pinched between the blades. Pinching is extremely painful for patients and difficult for the operator to avoid without removing the speculum in an open position, which causes significant discomfort to the patients as well. There are no satisfactory solutions for these problems, resulting in tremendous patient discomfort with the entire speculum experience.

In an attempt to limit sidewall encroachment and allow for better visualization of the vaginal walls and cervix, operators may attempt to place condoms or portions of medical gloves over the speculum. This is an unsatisfactory and ineffective approach as condoms and gloves were not designed to support the internal pressure of the vaginal walls, but to be as thin as possible. Furthermore, using these solutions can result in both condoms and glove fingers, or torn portions of them, being left behind in the vaginal cavity following removal of the speculum. Alternatively, operators may choose to use larger speculums to provide a larger viewing/accessing window to compensate for tissue entering the side of the speculum between the blades. However, increasing the size of the speculum can provide discomfort to patients. Moreover, while there are now different sizes of speculums offered for an examination, it can be hard to determine the correct size for a patient as the size of the patient does not necessarily correlate with the size of the speculum that should be used.

An additional drawback to the traditional speculum design is that speculums are traditionally made of metal, though some made with disposable plastic have been increasing in use. When the speculum is made of metal, it can feel cold to the patient upon entry to the vaginal cavity, especially in comparison to the internal temperatures of the body, which can result in discomfort for the patient during the procedure. This may result in the patient tensing up and making the procedure more painful. Even when made of plastic, the design of the speculum is generally the same as the traditional design (but for some differences that may exist in the locking mechanisms, wall thicknesses, consistencies between the types of plastic, etc.), meaning that even plastic speculums may face some of the same drawbacks as traditional speculums.

Embodiments herein generally relate to applicators for accessories to improve speculum devices, components of the same, and methods of making and using the same. The accessories overcome many drawbacks of existing speculum devices, and the applicators enable practitioners to easily position the accessories on speculum devices for use during a medical procedure. In one aspect, an applicator is provided for easy positioning of a sleeve accessory, either on an existing speculum design or an updated speculum design, to cover an insertion portion of the speculum.

SUMMARY OF THE INVENTION

One embodiment relates to an applicator for positioning a sleeve accessory on a medical speculum. The applicator has a flat, oblong shape with a distal end and a proximal end, the proximal end being broader than the distal end. Additionally, the distal end includes a first prong and a second prong. At least a portion of the distal end of the applicator is configured to slide into a lumen of a sleeve accessory to facilitate positioning of the sleeve accessory on a medical speculum.

Another embodiment relates to a method for positioning a sleeve accessory on a medical speculum. The method includes providing a medical speculum with a pair of bills, providing a sleeve accessory having a cylindrical sleeve body defining a lumen, and providing an applicator having a flat, oblong shape with a distal end and a proximal end, the proximal end being broader than the distal end. The distal end of the applicator includes a first prong and a second prong. The first prong and the second prong are configured to be folded into a first pocket and a second pocket, respectively, the first pocket and the second pocket configured to receive the bills of the medical speculum. The method further includes positioning the lumen of the sleeve accessory about the distal end of the applicator, sliding the bills of the speculum between the first pocket and the second pocket of the applicator to position the bills of the speculum in the lumen of the sleeve accessory; and removing the applicator from the lumen of the sleeve accessory.

Another embodiment relates to a kit. The kit includes a sleeve accessory having a cylindrical sleeve body defining a lumen, wherein the sleeve accessory is configured to be positioned on an insertion portion of a medical speculum, and an applicator having a flat, oblong shape with a distal end and a proximal end, the proximal end being broader than the distal end. The distal end includes a first prong and a second prong. The applicator is configured to slide, by the distal end of the applicator, at least partially into the lumen of the sleeve accessory to facilitate positioning of the sleeve accessory on the insertion portion of the medical speculum.

BRIEF DESCRIPTION OF THE DRAWINGS

FIGS. 6A and 6B are bottom views of an applicator for a sleeve accessory, according to an example embodiment.

FIG. 6C is a top view of the applicator of FIGS. 6A and 6B positioned in a sleeve accessory, according to an example embodiment.

FIG. 7A is a side view of the applicator of FIGS. 6A-6C being used to position a sleeve accessory on a medical speculum, according to an example embodiment.

DETAILED DESCRIPTION

Figure 1:
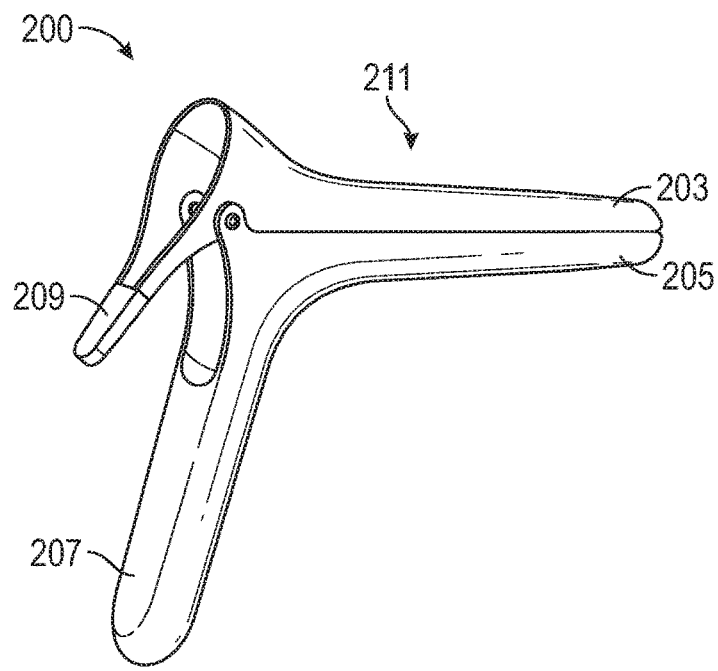
FIG. 1 is a side perspective view of a medical speculum on which a sleeve accessory according to various embodiments can be used.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented herein. It will be readily understood that the aspects of the present disclosure, as generally described herein and illustrated in the Figures, can be arranged, substituted, combined, and designed in a wide variety of different configurations, all of which are explicitly contemplated by and form part of this disclosure.

Referring to the Figures generally, an applicator for a sleeve accessory, or modifier sleeve, for a medical speculum is shown. The sleeve accessory may be used on any traditional speculum or any new or updated speculum design, including speculums that may be specifically designed for use with the sleeve accessory according to the present embodiments. The sleeve has an expandable body portion and is configured to be removably attached to an insertion portion of a speculum. In certain uses, a practitioner may be able to select a speculum with a narrower profile than the practitioner would regularly select because the sleeve reduces some of the previously described shortcomings of the traditional speculum design, for example, the problem of vaginal side wall tissue falling into the user's line of sight during use. The applicator is then used by the practitioner to easily and quickly position the sleeve accessory onto the bills of a speculum with minimal direct handling of the sleeve.

Referring now to FIG. 1, a two-blade speculum is shown according to certain traditional designs. As shown, the speculum 200 has an upper bill 203 and a lower bill 205, a handle 207, and a lever 209. The upper bill 203 and the lower bill 205 together comprise an elongated insertion portion 211. The insertion portion 211, which is expandable as described herein, may be inserted into the vaginal cavity of a female patient. During insertion, the upper bill 203 and the lower bill 205 are in a closed position, wherein there is a minimal amount of space between the two bills. Once inserted and in order to dilate the vaginal cavity, the bills 203 and 205 are separated into an open position by pressing the lever 209 towards the handle 207. In accordance with typical speculum designs, the speculum 200 may be made of any sturdy biomaterial including metals and plastics.

Figure 2:
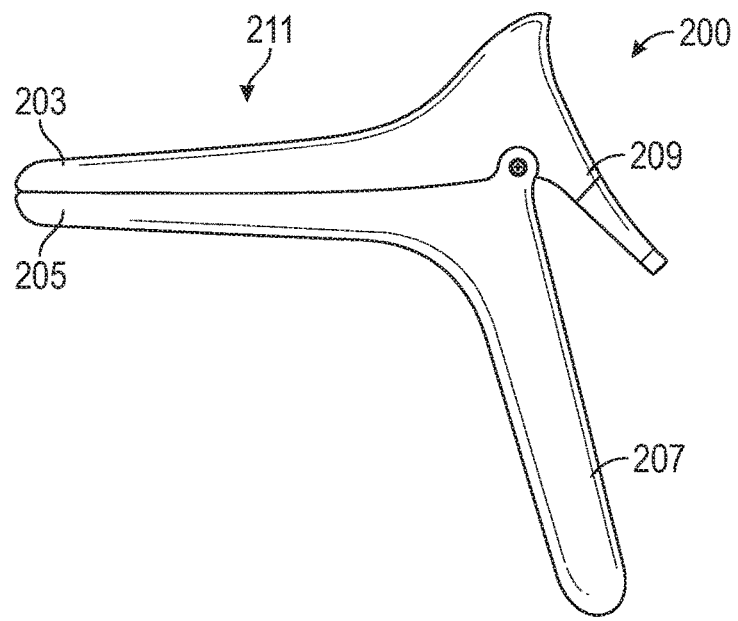
FIG. 2 is a side view of the medical speculum of FIG. 1.

Referring now to FIG. 2, a side view of speculum 200 is shown. The upper bill 203 and the lower bill 205 may be configured in such a way that when in the closed position, the upper bill 203 and the lower bill 205 are wider near the handle 207 than near a body or end of the insertion portion 211, i.e., the bills 203 and 205 distend quickly to create somewhat of a cone shape near the handle 207, as shown in the side view of FIG. 2. The bills 203 and 205 may maintain a constant shape after the cone, forming the elongated insertion portion 211. The upper bill 203 and the lower bill 205 of the elongated insertion portion 211 may have a uniform width or diameter as the bills 203 and 205 extend away from the handle 207. In other embodiments, the proximal portion of the bills 203 and 205 near the handle 207 may be up to two times wider than the distal end of the bills 203 and 205.

At a distal end of the elongated insertion portion 211, away from the proximal handle 207, the bills 203 and 205 may be rounded (e.g., the bills 203 and 205 may each be rounded, the ends of bills 203 and 205 closed together may form a rounded end, etc.). A rounded end may provide more comfort to a patient while receiving the speculum 200 in a cavity. The bills 203 and 205 may also be configured such that when in the closed position, the ends the bills 203 and 205 do not abut one another, creating a gap which helps to prevent tissue from becoming lodged in between the bills 203 and 205. In one embodiment, the bills 203 and 205 may be of the same length such that when the bills 203 and 205 are closed, they form a smooth, continuous end to the insertion portion 211. Alternatively, in another embodiment, one of the bills 203 and 205 may be longer than the other, such that when the bills 203 and 205 are in the closed position, the longer bill juts out from beneath or above the other bill.

As shown in FIG. 2, the handle 207 includes an upper portion and a lower portion. The upper portion of the handle 207 is coupled to bills 203 and 205. The lower portion provides a location for the user to hold the speculum 200. Coupled to the handle 207 is the lever 209. The lever 209 includes a mechanism for opening and closing bills 203 and 205. While the lever 209 is shown to be coupled to the upper portion of the handle 207, the lever 209 may be coupled to the handle 207 at any location. In some embodiments, the speculum 200 may also include a mechanism for locking the bills 203 and 205 into an open position.

Figure 3:
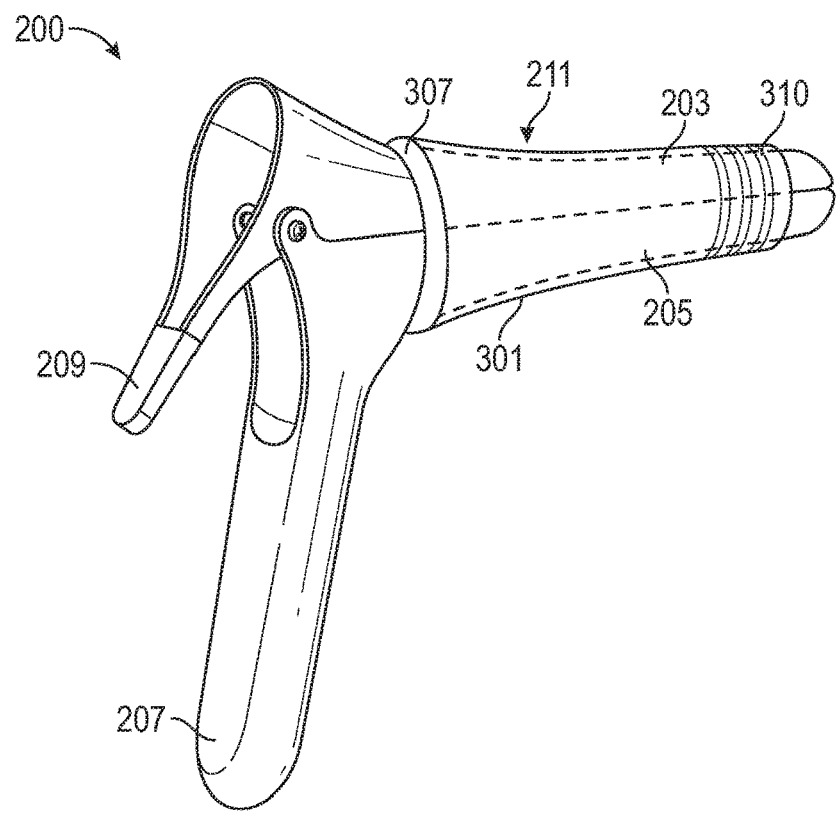
FIG. 3 is a side perspective view of a sleeve accessory positioned on a medical speculum, according to an example embodiment.

As described herein, using a sleeve accessory, such as sleeve accessory 301 shown in FIG. 3, with a medical speculum, such as speculum 200, may overcome the previously described shortcomings of the traditional speculum in a variety of ways. First, the sleeve may be made of a rubber or other soft material that is warmer than the traditional metal speculum bills. As such, inserting a speculum with a sleeve accessory attached may be less shocking, and thus more comfortable, to a patient than a bare metal speculum. The material may be at least substantially transparent to allow for good visualization of the vaginal cavity through the speculum with attached sleeve. Furthermore, a slimmer profile speculum can be utilized because of the sleeve (e.g., because the sleeve allows for improved visualization such that a larger speculum is not necessary), which provides better comfort for the patient during the procedure, examination, or surgery involving the speculum. The sleeve moreover allows the speculum to be removed in a closed position while preventing the pinching of either tissues or pubic hair during the process, significantly improving patient comfort while reducing patient anxiety. Importantly, the sleeve also provides the side wall support between the upper bill and the lower bill of the speculum that allows the practitioner better and less impeded visualization into the vagina and cervix. When used during an electrosurgery, the sleeve accessory may additionally provide insulation to protect the vaginal walls of a patient during the electrosurgery procedure. Accordingly, using a sleeve accessory with a medical speculum may provide a number of benefits to the patient. Because of this, it would also be advantageous to practitioners to have an applicator tool to help them in quickly and correctly positioning a sleeve accessory on a medical speculum. A sleeve accessory may be the same or similar to those described in U.S. patent application Ser. No. 15/393,041 filed Dec. 28, 2016, which is incorporated by reference herein in its entirety.

Though specific reference is made in this specification to the elements or features of speculum 200, it is understood that the accessory or modifier elements described herein, as well as any applicators for the accessory or modifier elements described herein, may be used with any speculum having an elongated and expandable insertion portion, such as any two-blade speculum design. The features herein used to describe speculum 200 may also be present on any other speculum on which the accessory or modifier elements described herein may be used.

In one aspect, a practitioner may use a sleeve accessory adapted to be used with a speculum, such as speculum 200, as follows. First, a user positions a sleeve accessory on an insertion portion of a speculum, such as insertion portion 211 on speculum 200, while the speculum is in a closed position. In exemplary embodiments, the user positions the sleeve accessory on the insertion portion by using an applicator tool, such as the applicators described herein, which aids the practitioner in quickly and correctly positioning the sleeve accessory on the insertion portion of the speculum. The user then inserts the speculum with the attached sleeve accessory into a patient's vagina. The user sets the speculum to the open position, thereby separating bills of the insertion portion and stretching the sleeve accessory. Next, the user performs a medical procedure on the patient using the speculum in the open position. The medical procedure may be any obstetric or gynecological procedure, such as an examination of the vaginal cavity, a Pap smear, an insertion or removal of an intrauterine device (IUD), an insemination, a sexually transmitted infection (STI) testing, a tissue collection, a biopsy, or an electrosurgery. After the user completes the medical procedure, the user closes the speculum and removes the speculum from the patient. Finally, the user removes the sleeve accessory from the speculum (e.g., by rolling the sleeve accessory off, by using a removal device, etc.).

Figure 4:
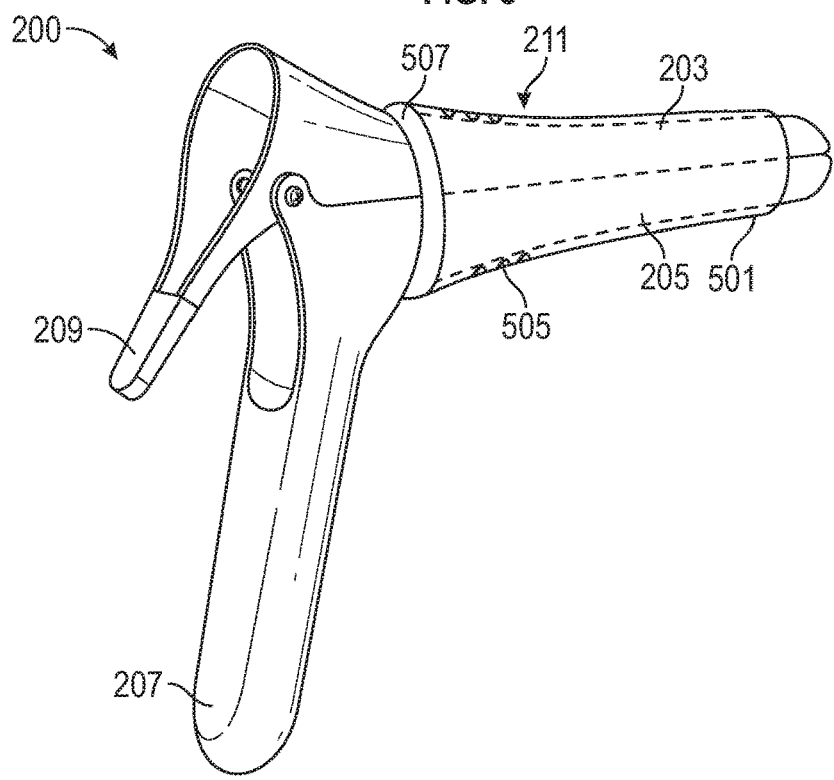
FIG. 4 is a side view of a sleeve accessory positioned on a medical speculum, according to an example embodiment.
Figure 5:
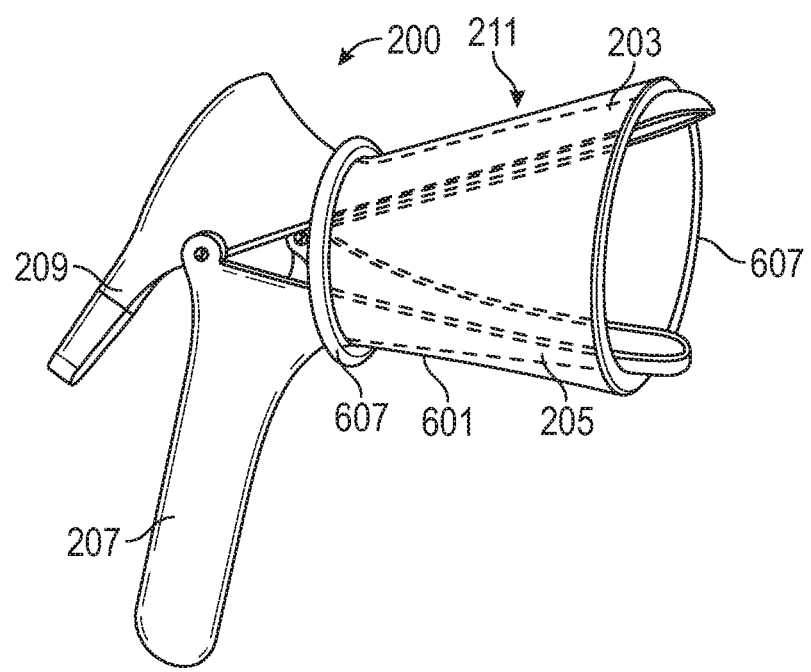
FIG. 5 is a side perspective view of a sleeve accessory positioned on a medical speculum in an open position, according to an example embodiment.

FIGS. 3-5 show examples of a sleeve accessory to be used with a speculum. The sleeve accessory may be the same or similar to those described in U.S. patent application Ser. No. 15/393,041 filed Dec. 28, 2016, which is incorporated by reference herein in its entirety. FIG. 3 depicts a sleeve accessory 301 on the elongated insertion portion 211 of speculum 200. As shown, the sleeve 301 is configured to be positioned on the elongated insertion portion 211, to surround or enclose both bills 203 and 205, while the bills are in a closed position. In some embodiments, the sleeve 301 has a cylindrical sleeve body. By "cylindrical" it is meant that the sleeve body has a continuous, longitudinal shape that surrounds a hollow area (e.g., a lumen or hollow sleeve channel) within an inner wall or surface of the cylinder. The cylindrical sleeve body is not limited to a circular cylinder and may instead have a cross-sectional shape that is a square, a rectangle, a circle, an oval, a triangle, and so on. In the embodiment shown, the sleeve 301 has a cylindrical shape with a proximal opening through which the insertion portion 211 can be inserted. In the embodiment shown, the shape of the sleeve 301 substantially matches the shape of the bills, or may be in another shape, on which the sleeve 301 is being positioned. As such, the cylindrical body of the sleeve 301 may have a uniform width or diameter between a distal end of the sleeve body and a proximal end of the sleeve body while the sleeve 301 is in an un-stretched or unexpanded state, to match a uniform width or diameter of the bills 203 and 205 extending away from the handle 207. In one embodiment, the uniform diameter of the cylindrical body of the sleeve 301 may range between 0.25 inches and 3.0 inches. In other embodiments, the sleeve 301 may comprise a different natural shape than the shape of the bills 203 and 205, and may also have a non-uniform width or diameter ranging between 0.25 and 3.0 inches when in an un-stretched or unexpanded state.

The sleeve 301 may be made of one or more compliant or partially compliant materials, such as latex, vinyl, natural and synthetic rubbers, silicone, nylon, polyethylene, polyurethane, polypropylene, and non-degradable or degradable elastomers. In preferred embodiments, the sleeve 301 may be made of a polyisoprene (PI), a polyurethane (PU), a thermoplastic polyurethane (TPU), a styrene copolymer (SBS), and/or a thermoplastic elastomer (TPE). The material of the sleeve 301 may range from completely transparent to translucent or frosty to opaque. Alternatively, the sleeve 301 may include a finish that ranges from completely transparent to translucent or frosty to opaque. Different finishes may be used for different types of gynecological examinations or procedures. For example, a thicker and/or more opaque sleeve may be used for a surgical procedure, such as an electrosurgery, while a thinner and/or more clear sleeve may be used for a gynecological examination or procedure.

The sleeve 301 or a portion of the sleeve 301 may optionally be coated with one or more bioactive or therapeutic agents, lubricants, or surface finishes. Examples of suitable bioactive or therapeutic agents include, but are not limited to, hormonal and non-hormonal contraceptive agents, cancer screening agents, vaginal spermicides, vaginal microbicides, antibacterial agents, antifungal agents, antiviral agents, anti-HIV agents, and cancer treatment agents, or combinations thereof. The bioactive or therapeutic agents may be in any suitable formulation that may be applied to the surface of a vaginal speculum, such as a liquid, gel and powder.

In some embodiments, lubricants may be applied to at least a portion of an inner surface of the sleeve 301 and/or to an outer surface of the sleeve 301. When applied to the inner surface of the sleeve 301, the lubricant may, e.g., aid in positioning the sleeve 301 on the insertion portion 211. When applied to an outer surface of the sleeve, the lubricant may, e.g., help the speculum 200 with the attached sleeve 301 be more easily inserted into the patient. In other embodiments, the lubricant on the interior surface and/or exterior surface of the sleeve 301 may instead be, or may be combined with, a powder applied to the sleeve 301 or a surface texture finished into a material of the sleeve 301. The powder and/or surface texture may likewise, e.g., aid the user in positioning the sleeve 301 on the insertion portion 211, help the speculum 200 with the attached sleeve 301 be more easily inserted into the patient, and so on. In various embodiments, the sleeve 301 may come with lubricant and/or powder pre-applied, the sleeve 301 may come in a kit with lubricant and/or powder included for the user to apply to the sleeve 301, the sleeve 301 may come with instructions that recommend types or brands of lubricants and/or powders for the user to apply to create the beneficial effects discussed above, etc.

As shown in FIG. 3, once positioned on the insertion portion 211, the sleeve 301 surrounds the bills 203 and 205 and preferably has a snug fit around bill 203 and 205. As such, sleeve 301 should not move along the bills 203 or 205 during insertion into the vagina or during a medical examination, procedure, or surgery being conducted on the vaginal or surrounding tissues. The sleeve 301 may additionally include ribbed details 310 that help the sleeve 301 remain securely fastened onto the insertion portion 211. In one embodiment, the ribbed details may be limited to a portion of the sleeve 301 secured to the smaller, narrower, distal end of the insertion portion 211. In other embodiments, the ribbed details may, additionally or alternatively, be limited to a portion of the sleeve 301 secured to the larger, proximal end of the insertion portion 211 near the handle 207, or be distributed throughout the length of the sleeve 301. In some embodiments, the ribbed details may instead be, or may be combined with, texture differences or lubrication differences provided on an inner surface of the sleeve 301 and/or gripping elements (e.g., such as flanges 505 shown in FIG. 4) positioned on an inner surface of the sleeve 301 that may help the sleeve 301 remain securely fastened onto the insertion portion 211.

The proximal opening of the sleeve 301, as well as a distal opening included in some embodiments of the sleeve 301, may have a ridged finish, shown as end ring 307. The ridged finish may be provided to give the user a ridge to aid the user in positioning the sleeve 301 on the insertion portion 211, to finish the end of the sleeve 301 so that the end of the sleeve 301 is less easily ripped or otherwise damaged, to provide additional tension to adhere the sleeve 301 to the insertion portion 211, and so on. The ridged finish may be provided as an end ring 307, which may be a rolled bead edge (i.e., similar to a condom) or may be formed from an encapsulated ring (i.e., a ring that is rolled into the end of the sleeve 301 and cured). In other embodiments, the ridged finish may be provided as a dip in the material of the sleeve 301, a secondary dip in another polymer material (e.g., of a different thickness, durometer, color, etc.) attached to the sleeve 301, an otherwise attached or adhered secondary material that finishes the opening(s), and so on.

FIG. 4 illustrates another embodiment of a sleeve accessory for a medical speculum, shown as sleeve 501. Sleeve 501 is designed similarly to sleeve 301, with a cylindrical sleeve body configured to be slid over an insertion portion of a speculum, such as insertion portion 211 of speculum 200. Sleeve 501 may have many of the same features as described above with respect to sleeve 301, such as an end ring 507. Sleeve 501 also includes flanges 505 to help the sleeve remain securely fastened onto the insertion portion 211. As shown in FIG. 4, similar to sleeve 301, the cylindrical body of sleeve 501 has an open proximal end and an open distal end. However, in some embodiments, a sleeve accessory may instead have a closed distal end (e.g., the sleeve 501 may wrap around the distal end of the bills 203 and 205 so as to enclose the top portion of the bills 203 and 205, or extend up to the distal end of the bills 203 and 205). In these embodiments, the sleeve accessory may further include a small hole or aperture (not shown) in the closed, distal end of the sleeve accessory, which may allow for visualization, tissue sampling, etc. through the otherwise closed distal end. Additionally, as shown in FIG. 4, the distal end of the sleeve 501 nearly reaches the distal end of the bills 203 and 205. However, in other embodiments, a sleeve accessory may not reach the end of the bills 203 and 205 when the sleeve accessory is positioned on the bills 203 and 205 or may extend past the end of the bills 203 and 205.

FIG. 5 illustrates a sleeve accessory, shown as sleeve 601, positioned on speculum 200. Sleeve 601 is configured similarly to sleeves 301 and 501 discussed above, with a cylindrical sleeve body surrounding a lumen configured to receive an insertion portion of a speculum, such as insertion portion 211 of speculum 200, and open proximal and distal ends framed by end rings 607. As shown in FIG. 5, once positioned on the speculum 200, when a force is applied to the lever 209 and the bills 203 and 205 of the speculum 200 separate, the sleeve 601 expands from a first state to a second state (i.e., from an unexpanded state to an expanded state). When the bills 203 and 205 separate, the sleeve 601 may stretch to accommodate the increase in distance between bills 203 and 205. Beneficially, the expansion of the sleeve 601 provides side wall retention for tissue encroachment from the side walls of the vagina, allowing the user to maintain an uninterrupted view of the vaginal cavity and cervix while viewing the vaginal cavity and cervix through the speculum 200. The expansion of the sleeve 601 also works to prevent vaginal tissue or pubic hair from entering the opening between the bills 203 and 205, as the bills 203 and 205 may cause pinching of the tissue or pubic hair that is painful for the patient when the bills 203 and 205 are returned to the closed position at the conclusion of the procedure, examination, or surgery. Additionally, when the bills 203 and 205 are closed, the sleeve 601 may return to its original state (e.g., the first state).

FIGS. 6A-6C illustrate an applicator 700 for a sleeve accessory (e.g., sleeve accessory 301, 501, and/or 601), according to one embodiment. The applicator 700 is used by a practitioner to facilitate the positioning of a sleeve accessory onto a medical speculum, such as speculum 200. A bottom view of the applicator 700 is shown in FIGS. 6A and 6B. As illustrated in FIG. 6A, according to one embodiment, the applicator 700 is flat and roughly oblong, with a broader proximal end 702 and a narrower distal end 704. The proximal end includes a tab 706 that may be pulled away from the main body of the applicator 700, while the distal end 704 splits into a first prong 708 and a second prong 710.

The applicator 700 further includes a first flap 712 and a second flap 714 formed into the sides of the applicator 700, where the first flap 712 is configured to fold at a first fold line 716 and the second flap 714 is configured to fold at a second fold line 718, as shown by the arrows of FIG. 6A. FIG. 6B illustrates the applicator 700 with the first flap 712 folded over the first fold line 716 and the second flap 714 folded over the second fold line 718. As shown in FIG. 6B, when the flaps 712 and 714 are folded over, the first flap 712 forms a first pocket 720 within the first prong 708 and the second flap 714 forms a second pocket 722 within the second prong 710.

The applicator 700 may be made of a stiff, noncompliant or minimally compliant material or of a flexible, more compliant material. Thus, the applicator 700 may be made of paper, cardboard, paperboard, or corrugated fiberboard. Alternatively, the applicator 700 may be made of natural or synthetic rubbers or of a plastic, such as latex, vinyl, silicone, polyethene, polyurethane, polypropylene, polycarbonate, or non-degradable or degradable elastomers. In some embodiments, the applicator 700 may be designed for a single use and be disposable. In other embodiments, the applicator 700 may be designed to be reusable (e.g., be designed to be sterilizable for reuse).

A top view of the applicator 700 positioned within a sleeve accessory, shown as sleeve 801, is illustrated in FIG. 6C. The sleeve 801 is designed similarly to sleeves 301, 401, 501, and 601, with a cylindrical sleeve body configured to be slid over an insertion portion of a speculum, such as insertion portion 211 of speculum 200. The sleeve 801 further includes an open proximal end 802 framed by an end ring 807 and an open distal end 804. However, other embodiments of sleeve 801 may include a closed distal end, one or more gripping elements (e.g., similar to ribbed details 310 or flanges 505), one or more coatings, one or more surface finishes, and so on, as described above with respect to sleeves 301, 501, and 601.

As illustrated in FIG. 6C, the applicator 700 is positioned within the sleeve 801. In an exemplary embodiment, the applicator 700 and the sleeve 801 are packaged together with the applicator 700 pre-inserted into the sleeve 801 as shown in FIG. 6C. However, in other embodiments, a user may need to slide or otherwise position the applicator 700 into the sleeve 801. In various embodiments, as shown, the applicator 700 is designed such that the oblong shape of the applicator 700, with the broader proximal end 702 narrowing to the distal end 704, fits the shape of the sleeve 801, which may also narrow from the broader proximal end 802 to the narrower distal end 804. Accordingly, the applicator 700 may be easily positioned within the sleeve 801 until the prongs 708 and 710 abut the walls of the sleeve 801. In some embodiments, the prongs 708 and 710 may create friction between the applicator 700 and walls of the sleeve 801 such that there is at least some resistance to the applicator 700 being slid out from the sleeve 801. Additionally, the tab 706 is configured to be tucked over the top edge (e.g., over the end ring 807) of the proximal end 802 of the sleeve 801 once the applicator 700 has been slid into the sleeve 801. Thus, the tab 706 and/or the resistance created by friction between the prongs 708 and 710 and the walls of the sleeve 801 may prevent the applicator 700 from inadvertently sliding out of the sleeve 801. Instead, once the applicator 700 is inserted into the sleeve 801, at least a small force may need to be applied to remove the applicator 700 from the sleeve 801.

Additionally, the prongs 708 and 710 are configured such that when the applicator 700 is inserted into the sleeve 801, the prongs 708 and 710 hold the interior of the sleeve 801 at least partially open. In this way, the prongs 708 and 710 allow a user to easily slide an insertion portion of a medical speculum into the interior of sleeve 801. Furthermore, the prongs 708 and 710 are spaced apart such that the space between the first fold line 716 and the second fold line 718 are at least as wide as the insertion portion of the medical speculum. As such, the insertion portion may be slid in between the prongs 708 and 710 and through the pockets 720 and 722 formed in the prongs 708 and 710. Thus, the prongs 708 and 710 of the applicator 700 may guide the insertion portion of the medical speculum into the lumen of sleeve 801.

As shown in FIG. 6C, in some embodiments, the distal ends 704 of the prongs 708 and 710 may not reach the distal end 804 of the sleeve 801. However, in other embodiments, the applicator 700 may be configured such that the ends of the prongs 708 and 710 meet the distal end 804 of the sleeve 801, or the applicator 700 may be configured such that the ends of the prongs 708 and 710 extend past the distal end 804 of the sleeve 801.

FIGS. 7A-7D illustrate a process of using the applicator 700 to position the sleeve 801 on a medical speculum, such as speculum 200. First, the user removes an applicator 700 and a sleeve 801 from packaging intended to keep the sleeve 801 sterile. In exemplary embodiments, the applicator 700 and the sleeve 801 are packaged together with the applicator 700 pre-inserted into the sleeve 801 (e.g., as shown in FIG. 6C). In such embodiments the user may, for example, remove the applicator 700 and sleeve 801 combination from the packaging by grasping the broad, proximal end 702 of the applicator and pulling the applicator 700 and sleeve 801 combination from the packaging. In this way, the user may remove the applicator 700 and sleeve 801 from the packaging without directly handling the sleeve 801, which may help keep the sleeve 801 sterile. However, in other embodiments, the applicator 700 and the sleeve 801 may be packaged in separate packaging or may be packaged together but without the applicator 700 pre-inserted into the sleeve 801. In such embodiments, the user may remove the applicator 700 and the sleeve 801 from the packaging and insert the applicator 700 (e.g., by the distal end 704 of the applicator 700) at least partially into the sleeve 801, as shown in FIG. 6C.

Figure 7B:
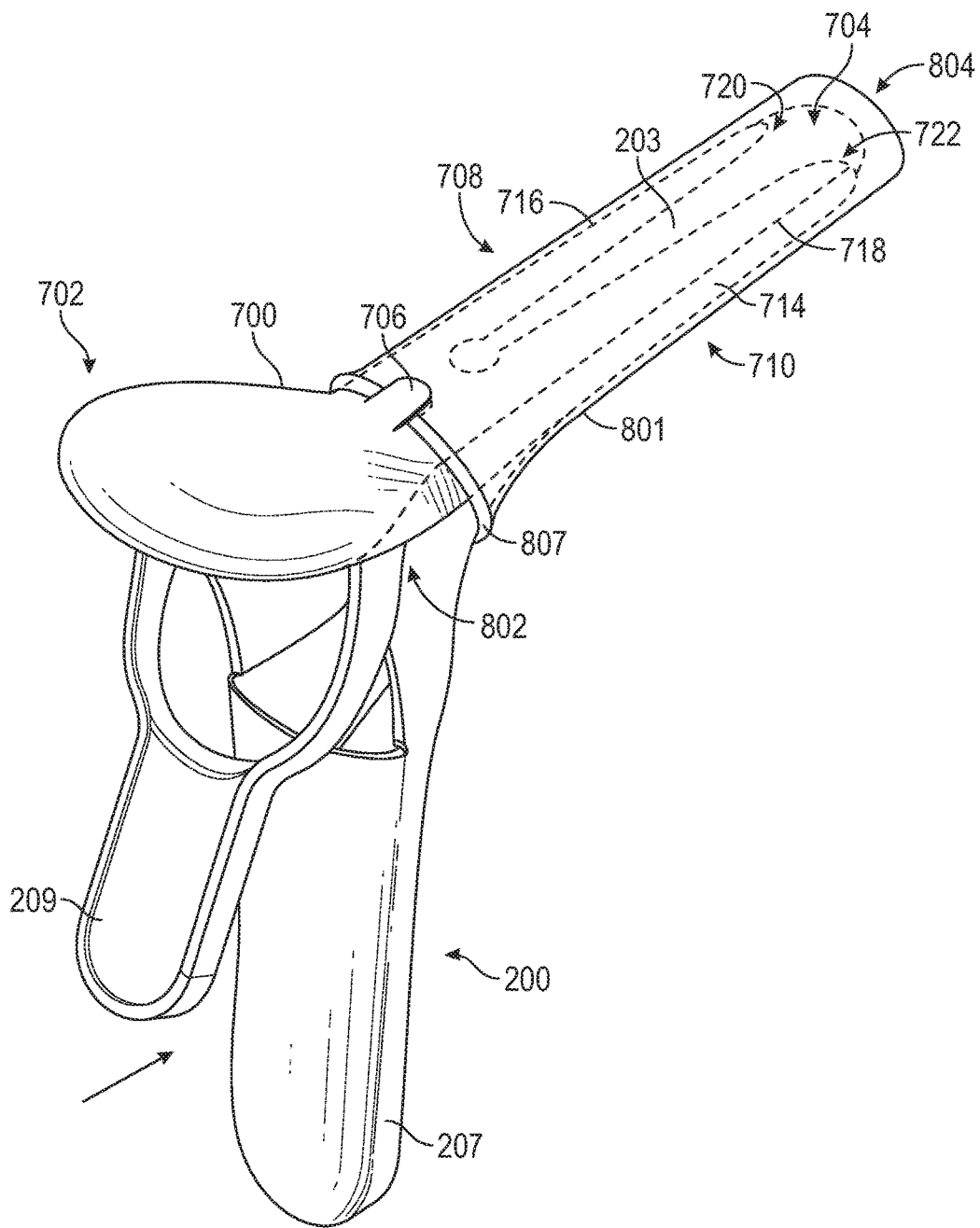
FIG. 7B is a top perspective view of the applicator of FIGS. 6A-6C being used to position a sleeve accessory on a medical speculum, according to an example embodiment.

With the applicator 700 positioned in the sleeve 801, the prongs 708 and 710 of the applicator 700 hold the interior of the sleeve 801 at least partially open. Further, the applicator 700 should not inadvertently slide out of the sleeve 801 once inserted into the sleeve 801. Thus, the user then grasps the applicator 700 by the broad, proximal end 702, thereby holding the sleeve 801. Next, holding the speculum 200 by the handle 207, the user inserts the insertion portion 211 of the speculum 200 into the lumen of the sleeve 801 through the proximal end 802 of the sleeve 801. FIGS. 7A and 7B illustrate the insertion portion 211 of the speculum 200 being inserted into the sleeve 801, with FIG. 7A showing a side view of the speculum 200 being inserted into the sleeve 801 and FIG. 7B showing a top perspective view of the speculum 200 being inserted into the sleeve 801. In FIGS. 7A and 7B, the speculum 200 is inserted by pushing the sliding the speculum 200 into the sleeve 801 in the direction of the arrows shown in FIGS. 7A and 7B. Further, as shown in FIGS. 7A and 7B, the applicator 700 is designed such that the insertion portion 211 may be inserted in between the prongs 708 and 710 and through the pockets 720 and 722 created by the prongs 708 and 710, such that the flaps 712 and 714 envelop the sides of the bills 203 and 205 once speculum 200 is inserted.

Figure 7C:
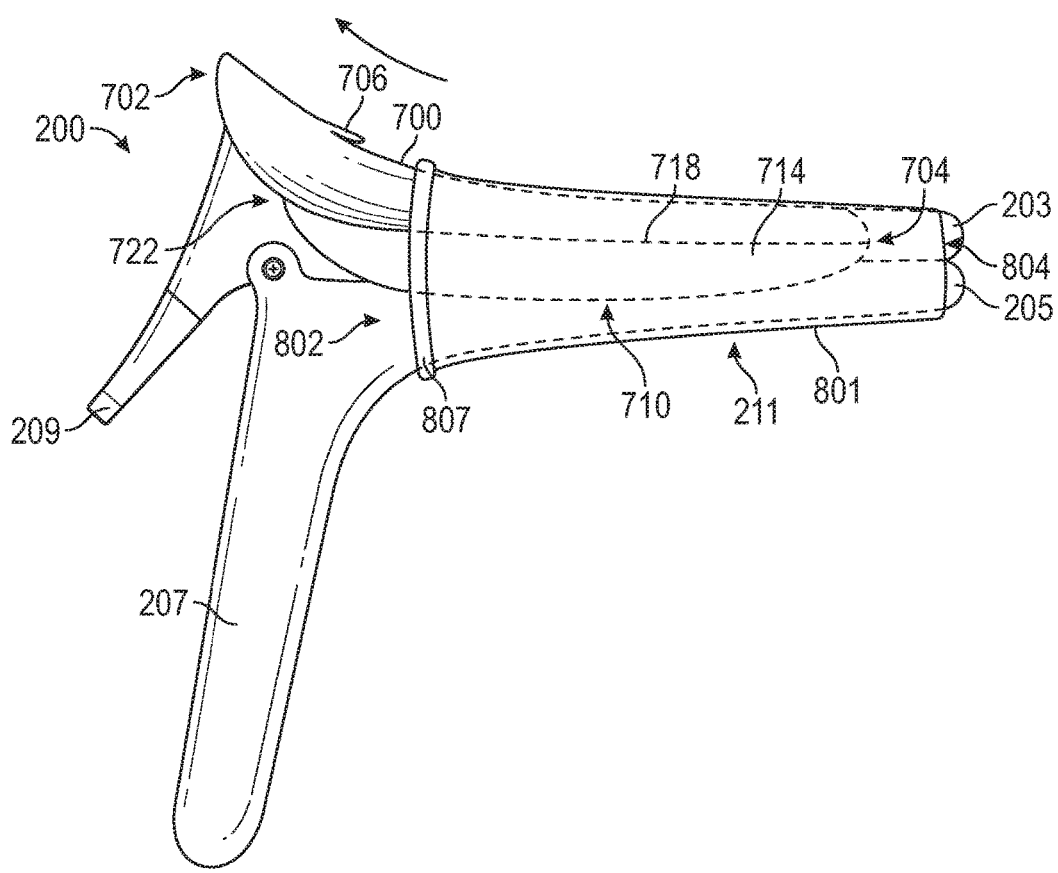
FIG. 7C is a side view of the applicator of FIGS. 6A-6C being used to position a sleeve accessory on a medical speculum, according to an example embodiment.
Figure 7D:
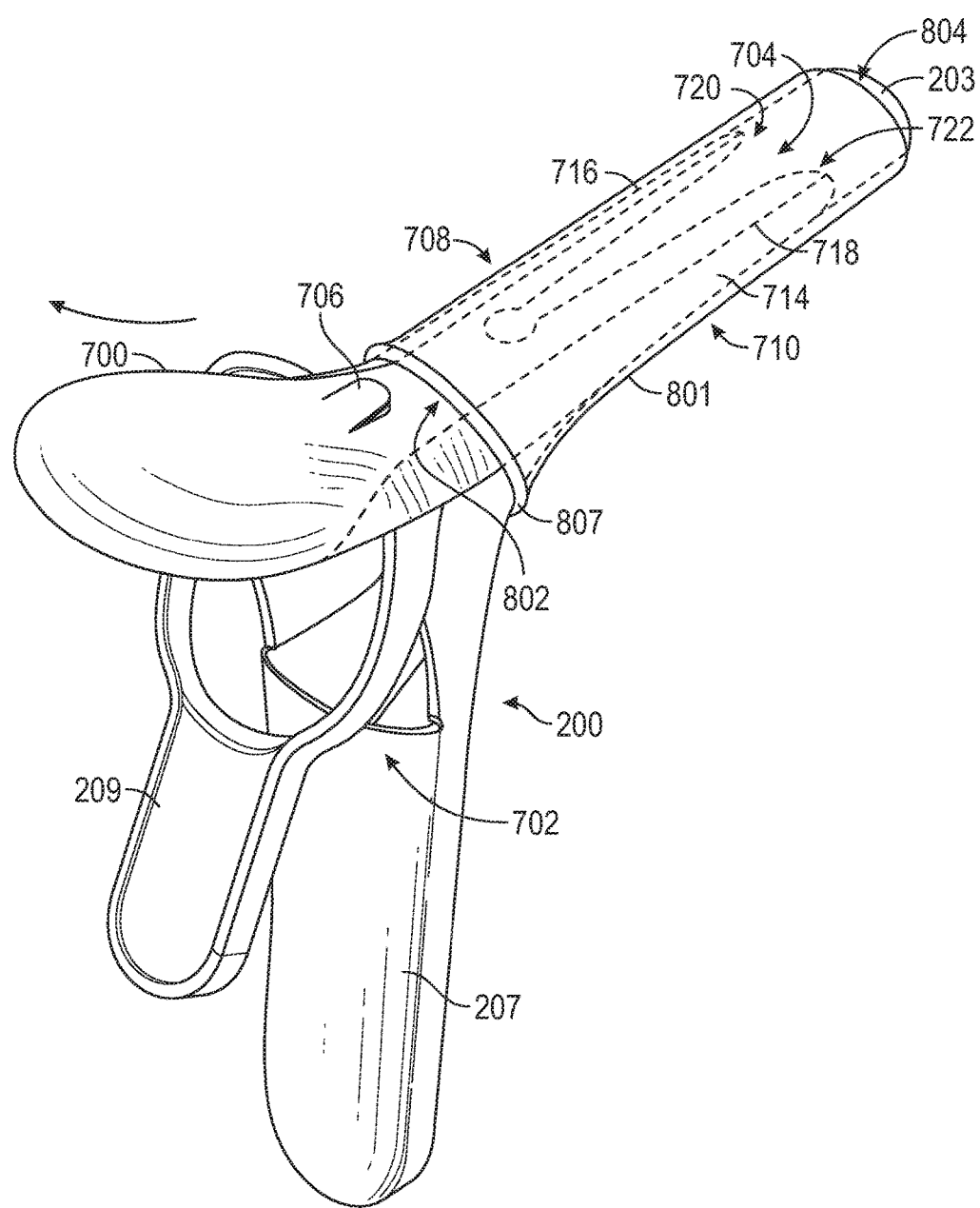
FIG. 7D is a top perspective view of the applicator of FIGS. 6A-6C being used to position a sleeve accessory on a medical speculum, according to an example embodiment.

Once the insertion portion 211 has been inserted into the lumen of the sleeve 801, the user grasps the proximal end 702 of the applicator 700 and, still holding the speculum 200 by the handle 207, pulls the applicator 700 out from the lumen of the sleeve 801. FIGS. 7C and 7D illustrate the applicator 700 being removed from the sleeve 801, with FIG. 7C showing a side view of the speculum 200 with the applicator 700 being removed and FIG. 7D showing a top perspective view of the speculum 200 with the applicator 700 being removed. The applicator 700 is removed in the direction of the arrows shown in FIGS. 7C and 7D. As discussed above, once inserted into the sleeve 801, friction may exist between the prongs 708 and 710 of the applicator 700 and the walls of the sleeve 801. Thus, when the applicator 700 is removed from the sleeve 801, this friction may pull the sleeve 801 more fully and more securely onto the insertion portion 211 of the speculum 200. For example, by comparing FIGS. 7A and 7B with FIGS. 7C and 7D, one can see that the act of pulling the applicator 700 out from the sleeve 801 has caused the distal end 804 of the sleeve 801 to be pulled past the distal ends of the bills 203 and 205. The user continues to pull the applicator 700 until it is completely removed from the sleeve 801, at which point the sleeve 801 is fully positioned on the insertion portion 211 of the speculum 200.

In some embodiments, an applicator (e.g., applicator 700), a sleeve accessory (e.g., sleeve accessory 301, 501, 601, or 801), and/or a medical speculum (e.g., speculum 200) may be provided in a kit form. In one embodiment, the kit may include one applicator, one accessory sleeve, and/or one speculum. In another embodiment, the kit may include a plurality of speculums of varying lengths and widths and of varying expansion capabilities (i.e., capable of opening the bills in different ways, to different opening lengths, etc.), one or more sleeves configured to fit the plurality of speculums, and one or more applicators configured to fit the one or more sleeves and position the one or more sleeves on the one or more speculums. In yet another embodiment, the kit may further include accessories related to the needs of the examination procedure, for example, an IUD insertion device, a disposable electrosurgery tool, etc. In yet another embodiment, a plurality of applicators can be provided loosely in a large package or box.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A device comprising:
a medical speculum;
a sleeve accessory having a cylindrical sleeve body defining a lumen, the sleeve accessory positioned on an insertion portion of the medical speculum; and
an applicator within the lumen of the sleeve accessory, the applicator having a distal end and a proximal end, the proximal end being broader than the distal end, the distal end of the applicator comprising a first prong and a second prong, wherein at least a portion of the distal end of the applicator slides into the lumen of the sleeve accessory, and wherein the applicator within the lumen of the sleeve accessory is configured to receive the medical speculum to facilitate positioning of the sleeve accessory on the medical speculum, wherein the first prong and the second prong of the applicator are folded into a first pocket and a second pocket, respectively, and wherein the first pocket and the second pocket are configured to receive the medical speculum and thereby guide the medical speculum into the lumen of the sleeve accessory.

2. The device of claim 1, wherein the first prong and the second prong of the applicator are spaced apart such that, once the applicator has been slid at least partially into the lumen of the sleeve accessory, the first prong and the second prong abut inner walls of the sleeve accessory.

3. The device of claim 1, wherein the proximal end of the applicator includes a tab, and wherein the tab is configured to be tucked over a proximal end of the sleeve accessory.

4. The device of claim 1, wherein the applicator is disposable.

5. The device of claim 1, wherein the applicator is made of a rubber, plastic, paper or cardboard material.

6. The device of claim 1, wherein the sleeve accessory is disposable.

7. The device of claim 1, wherein the sleeve accessory is made of latex, vinyl, natural rubber, synthetic rubber, silicone, nylon, polyethylene, polyurethane, polypropylene, non-degradable elastomer, or degradable elastomer.

8. A device comprising:
a sleeve accessory having a cylindrical sleeve body defining a lumen, the sleeve accessory configured to be positioned on an insertion portion of a medical speculum;
an applicator within the lumen of the sleeve accessory, the applicator having a distal end and a proximal end, the proximal end being broader than the distal end, the distal end comprising a first prong folded into a first pocket and a second prong folded into a second pocket, at least a portion of the distal end of the applicator configured to slide into the lumen of the sleeve accessory, the applicator within the lumen of the sleeve accessory configured to receive the medical speculum to facilitate positioning of the sleeve accessory on the medical speculum, and the first pocket and the second pocket configured to receive the medical speculum and thereby guide the medical speculum into the lumen of the sleeve accessory.

9. The device of claim 8, wherein the first prong and the second prong are spaced apart such that, once the applicator has been slid at least partially into the lumen of the sleeve accessory, the first prong and the second prong abut inner walls of the sleeve accessory.

10. The device of claim 8, wherein the proximal end of the applicator includes a tab, and wherein the tab is configured to be tucked over a proximal end of the sleeve accessory.

11. The device of claim 8, wherein the applicator is disposable.

12. The device of claim 8, wherein the applicator is made of a paper or cardboard material.

13. The device of claim 8, wherein the sleeve accessory is disposable.

14. The device of claim 8, wherein the sleeve accessory is made of latex, vinyl, natural rubber, synthetic rubber, silicone, nylon, polyethylene, polyurethane, polypropylene, non-degradable elastomer, or degradable elastomer.

* * * * *